(12) United States Patent
Yomota et al.

(10) Patent No.: US 11,537,207 B2
(45) Date of Patent: Dec. 27, 2022

(54) TACTILE STIMULUS PRESENTATION DEVICE

(71) Applicant: SHIMADZU CORPORATION, Kyoto (JP)

(72) Inventors: Satoshi Yomota, Kyoto (JP); Shin Nakamura, Kyoto (JP); Rintaro Yamamoto, Kyoto (JP); Ayaka Hori, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 364 days.

(21) Appl. No.: 16/744,316

(22) Filed: Jan. 16, 2020

(65) Prior Publication Data

US 2020/0249760 A1    Aug. 6, 2020

(30) Foreign Application Priority Data

Jan. 31, 2019    (JP) .............................. JP2019-015800

(51) Int. Cl.
*G06F 3/01*    (2006.01)
*A61B 5/00*    (2006.01)
(Continued)

(52) U.S. Cl.
CPC ............ *G06F 3/016* (2013.01); *A61B 5/0053* (2013.01); *A61B 5/162* (2013.01); *A61B 5/4088* (2013.01); *G08B 6/00* (2013.01)

(58) Field of Classification Search
CPC ..... A61B 5/0053; A61B 5/4088; A61B 5/162; G09B 21/004; G08B 6/00; G06F 3/016
See application file for complete search history.

(56) References Cited

U.S. PATENT DOCUMENTS

| | | | |
|---|---|---|---|
| 7,233,315 B2* | 6/2007 | Gregorio | G06F 3/016 345/164 |
| 7,336,260 B2* | 2/2008 | Martin | G09B 21/003 345/169 |

(Continued)

FOREIGN PATENT DOCUMENTS

| | | |
|---|---|---|
| DE | 19517649 A1 | 11/1996 |
| JP | 2005-328270 A | 11/2005 |
| WO | 2012/077313 A1 | 6/2012 |

OTHER PUBLICATIONS

Communication dated Dec. 8, 2021, from the European Patent Office in European Application No. 20 150 980.9.

(Continued)

*Primary Examiner* — Vinh T Lam
(74) *Attorney, Agent, or Firm* — Sughrue Mion, PLLC

(57) ABSTRACT

A tactile stimulus presentation device includes a stage, a contact member, a drive mechanism, an information setting part, and a control part. The stage includes an opening and an arrangement surface, the arrangement surface on which a body part of a subject is arranged thereon so as to close the opening. The contact member is for giving a tactile stimulus to the subject by being in contact with the body part of the subject arranged on the arrangement surface of the stage through the opening. The drive mechanism is a mechanism for holding the contact member and moving the contact member in a direction substantially parallel to the arrangement surface and in a direction substantially perpendicular to the arrangement surface. The information setting part is configured to set information to be presented by gibing tactile stimulation to the subject by tactile stimulation. The control part is configured to control the drive mechanism to present the information set by the information setting part by giving tactile stimulation to the body part of the subject arranged in abutment on the arrangement surface.

11 Claims, 3 Drawing Sheets

(51) Int. Cl.
*A61B 5/16* (2006.01)
*G08B 6/00* (2006.01)

(56) References Cited

U.S. PATENT DOCUMENTS

| | | | | |
|---|---|---|---|---|
| 9,030,306 B2* | 5/2015 | Lim | ........................ | G06F 3/016 |
| | | | | 340/407.1 |
| 9,030,424 B2* | 5/2015 | Shih | ................... | G06F 3/04886 |
| | | | | 345/173 |
| 9,812,033 B2* | 11/2017 | Chari | ................... | G09B 21/004 |
| 9,965,036 B2* | 5/2018 | Deokar | ................ | G06F 3/0445 |
| 10,121,335 B2* | 11/2018 | Deokar | ................ | G09B 21/004 |
| 10,423,233 B2* | 9/2019 | Dillon, Jr. | ............... | G06F 3/041 |
| 10,437,337 B2* | 10/2019 | Park | ..................... | G09B 21/003 |
| 10,635,175 B2* | 4/2020 | Krumpelman | ...... | G06F 3/03547 |
| 10,775,894 B2* | 9/2020 | Maalouf | ............... | G06N 20/00 |
| 10,854,108 B2* | 12/2020 | Chen | ....................... | G06F 3/167 |
| 10,965,464 B1* | 3/2021 | Reddy | .................... | G06F 21/31 |
| 11,009,953 B2* | 5/2021 | Hashimoto | ........... | G06F 3/0202 |
| 11,011,032 B2* | 5/2021 | Do | .......................... | G06F 3/016 |
| 11,327,648 B2* | 5/2022 | Dascola | ................. | G06F 3/0233 |
| 2012/0214139 A1* | 8/2012 | Murphy | ............... | G09B 21/003 |
| | | | | 434/114 |
| 2013/0088341 A1* | 4/2013 | Lim | ........................ | G06F 3/016 |
| | | | | 340/407.1 |
| 2013/0252215 A1 | 9/2013 | Wu et al. | | |
| 2018/0081439 A1* | 3/2018 | Daniels | ................... | G06F 1/163 |
| 2018/0315342 A1* | 11/2018 | Chari | ................... | G09B 21/004 |
| 2020/0293111 A1* | 9/2020 | Gwak | ..................... | G06F 3/016 |
| 2021/0400248 A1* | 12/2021 | Blanke | ................ | H04N 13/117 |

OTHER PUBLICATIONS

Communication dated May 29, 2020, from the European Patent Office in European Application No. 20150980.9.
Office Action dated May 10, 2022 issued by the Japanese Patent Office in Japanese Application No. 2019-015800.
Communication dated Sep. 27, 2022 from the Chinese Patent Office in Chinese Application No. 202010071885.X.

* cited by examiner

TACTILE STIMULUS PRESENTATION DEVICE

BACKGROUND OF THE INVENTION

1. Field of the Invention

The present invention relates to a tactile stimulus presentation device for presenting a tactile stimulus to a subject in order to diagnose cognitive ability of the subject.

2. Description of the Related Art

Various diagnostic methods have been employed to diagnose cognitive ability of a subject. One of methods for diagnosing dementia is a method called Sumanu (スマヌ) method. In the Sumanu method, an experimenter presents tactile stimuli by writing Japanese characters "ス" (su), "マ" (ma), "ヌ" (nu) on the back or palm of a subject, and the subject answers the characters presented by the experimenter. By analyzing a correct answer rate and a state of cerebral blood flow when the stimuli are presented, presence or absence of dementia or mild cognitive impairment is determined.

As a method of diagnosing dementia, in addition to the method of presenting tactile stimuli as described above, there is a method of presenting auditory stimuli or visual stimuli to a subject, and a device for checking the presence or absence of development of dementia by presenting auditory stimuli or visual stimuli to a subject has also been proposed (see, for example, WO2012/077313A1).

SUMMARY OF THE INVENTION

The conventional Sumanu method has a problem in that a character shape and writing pressure differ by each experimenter who writes characters on the body of a subject, and this difference affects identification of characters. In order to make the tactile stimulus to be presented to the subject constant, a device has also been proposed that presents information such as characters to a subject by pressing a member having a surface on which a character, a symbol, or the like is represented by unevenness against a palm or finger of the subject. However, in such a device, the types of information that can be presented to the subject are limited. In order to increase the types of information to be presented, it is necessary to prepare uneven members according to the respective types of information, and such a device is not generally usable.

Accordingly, it is an object of the present invention to provide a device capable of accurately presenting various pieces of information to a subject by tactile stimulation.

The tactile stimulus presentation device according to the present invention includes a stage, a contact member, a drive mechanism, an information setting part, and a control part. The stage includes an opening and an arrangement surface on which a body part of a subject is arranged thereon so as to close the opening. The contact member is for giving a tactile stimulus to the subject by being in contact with the body part of the subject arranged on the arrangement surface of the stage through the opening. The drive mechanism is a mechanism for holding the contact member and moving the contact member in a direction substantially parallel to the arrangement surface and in a direction substantially perpendicular to the arrangement surface. The information setting part is configured to set information to be presented by giving tactile stimulation to the subject. The control part is configured to control the drive mechanism to present the information set by the information setting part by giving tactile stimulation to the body part of the subject arranged on the arrangement surface.

That is, the tactile stimulus presentation device according to the present invention presents information to a subject by arranging a body part of the subject on a stage, and moving a contact member through an opening provided in the stage, to thereby write information such as a character or symbol on the body part of the subject. Since desired information such as a character or symbol can be written on the body part of the subject by moving the contact member, various pieces of information can be accurately presented to the subject by contact stimulation.

Incidentally, since there are individual differences in sensitivity of tactile sense of a subject, when information is presented while the contact member is in contact with the body of the subject with the same contact pressure, a subject who can feel the contact of the contact member sufficiently and a subject who cannot exist, and it is conceivable that cognitive ability cannot be accurately determined.

Accordingly, the tactile stimulus presentation device may further include a contact pressure setting part configured to set a contact pressure by the contact member to the body part of the subject arranged on the arrangement surface, in which the control part is configured to control the drive mechanism so as to adjust a contact pressure by the contact member to the body part of the subject arranged in abutment on the arrangement surface to the contact pressure set by the contact pressure setting part. Thus, the contact pressure of the contact member to the body of a subject can be adjusted, and influence on a diagnosis by individual differences in sensitivity of tactile sense of the subject can be made small.

Further, the tactile stimulus presentation device may further include a speed setting part configured to set a speed at which the drive mechanism moves the contact member in a direction substantially parallel to the arrangement surface, in which the control part is configured to control the drive mechanism to move the contact member in a direction substantially parallel to the arrangement surface at the speed set by the speed setting part.

Further, when the body of a subject arranged on the stage arrangement surface is uneven, the contact member cannot continue to be in contact with the body of the subject normally during presentation of information to the subject, and it is conceivable that accurate information is not presented to the subject.

Accordingly, in the present invention, the contact member may be configured so that a tip thereof is elastically displaced by an external force in a direction substantially perpendicular to the arrangement surface. Thus, when information is presented to the subject by moving the contact member, a tip of the contact member can follow unevenness of the body of the subject, and accuracy of information presentation to the subject can be ensured.

Further, even the same body part differs in size depending on the subject. Accordingly, in the present invention, the stage may be formed by a plate supported at a predetermined position by a plate support part, and the plate supported by the plate support part is a plate arbitrarily selected from a plurality of types of plates having different sizes of the opening. Thus, the size of the opening can be adjusted by selecting a plate according to the subject. In this case, the tactile stimulus presentation device may further include a plate recognition part configured to recognize a type of the plate supported by the plate support part, and the control part is configured to control the drive mechanism so as to present, by giving tactile stimulation to a subject, information of a size corresponding to a size of the opening of the plate recognized by the plate recognition part. Then, since the device automatically recognizes the plate supported by the plate support part and performs an operation according to the size of the opening of the plate, the experimenter does not need to input information about the plate to the device.

In the above case, each of the plurality of types of plates may have a through hole at a different position thereof from each other or have a different number of through holes, and the plate recognition part can be configured to recognize a type of the plate supported by the plate support part by detecting the position of the through hole of the plate or the number of through holes of the plate supported by the plate support part by using a switch.

Further, the body part of the subject to be arranged on the arrangement surface may be a palm.

The tactile stimulus presentation device according to the present invention presents information to a subject by arranging a body part of a subject on a stage, and moving a contact member through an opening provided in the stage, to thereby write information such as a character or symbol on the body part of the subject. Thus, the tactile stimulus presentation device can accurately present various pieces of information to a subject by tactile stimulation.

BRIEF DESCRIPTION OF THE DRAWINGS

FIG. 3A illustrates a case where no external force acts on a tip portion, and FIG. 3B illustrates a case where an external force acts on the tip portion.

DETAILED DESCRIPTION OF THE INVENTION

Hereinafter, an embodiment of a tactile stimulus presentation device will be described with reference to drawings.

Figure 1:
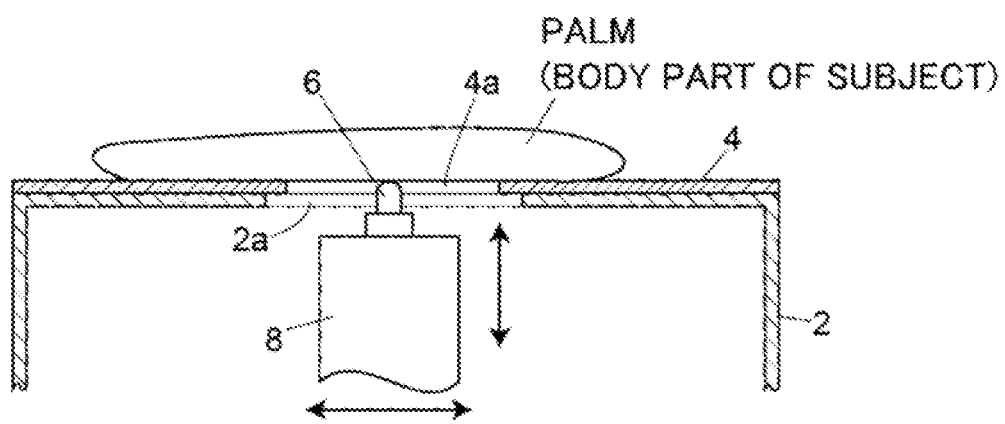
FIG. 1 is a schematic configuration view illustrating an embodiment of a tactile stimulus presentation device.

As illustrated in FIG. 1, the tactile stimulus presentation device includes a housing 2, a plate 4, a contact member 6, and a drive mechanism 8. The plate 4 has an opening 4a, and is disposed on an upper surface of the housing 2 so that the opening 4a is located above an opening 2a provided in an upper surface of the housing 2. The palm that is a body part of a subject is arranged on an upper surface of the plate 4 so as to close the opening 4a. That is, the upper surface of the plate 4 constitutes an arrangement surface for arranging a body part of a subject, the plate 4 constitutes a stage having the arrangement surface, and the housing 2 is a plate support part that supports the plate 4.

The contact member 6 is for giving a contact stimulus to the subject by being in contact with the palm of the subject arranged on the upper surface of the plate 4 through the openings 2a and 4a. The contact member 6 is held by the drive mechanism 8 with a spherical tip facing upward. The drive mechanism 8 is provided inside the housing 2, and has a mechanism for moving the contact member 6 in an X-axis direction and a Y-axis direction orthogonal to each other in an in-plane direction and a mechanism for moving the contact member 6 in a Z-axis direction that is a vertical direction. As the mechanisms for moving the contact member 6 in the X-axis direction, the Y-axis direction, and the Z-axis direction, besides a mechanism for moving a moving portion joined to a timing belt in one axis direction using rotation of the timing belt, there is one using a rack and pinion mechanism.

Figure 2:
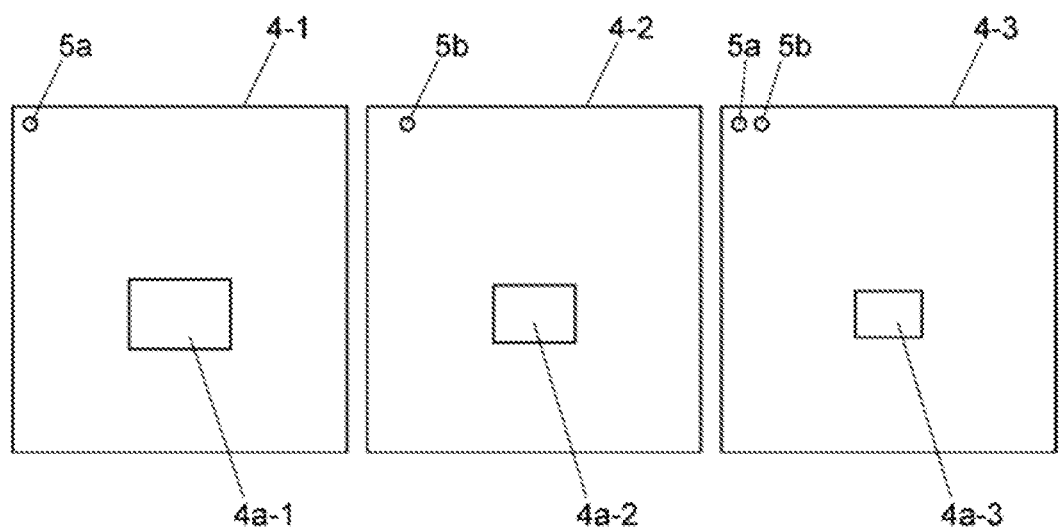
FIG. 2 is a plan view illustrating three types of plates used in the same embodiment.

The plate 4 on the housing 2 can be changed to another plate having a different size of the opening 4a. As illustrated in FIG. 2, in this embodiment, plates 4-1 to 4-3 having openings 4a-1 to 4a-3 of different sizes are prepared, and a plate 4 suitable for the subject can be arbitrarily selected from these three plates 4-1 to 4-3 and placed on the housing 2.

Through holes 5a and/or 5b for individual recognition are provided at corners of the respective plates 4-1 to 4-3. Although not illustrated in FIG. 1, a switch 12 (see FIG. 4) for detecting presence or absence of the through holes 5a and 5b of the plate 4 placed on the housing 2 is provided in the housing 2. As will be described later, the tactile stimulus presentation device of this embodiment has a function to recognize which of the plates 4-1 to 4-3 is the plate 4 placed on the housing 2 using a signal of the switch 12. In the example of FIG. 2, only the through hole 5a is provided at a corner of the plate 4-1, only the through hole 5b is provided at a corner of the plate 4-2, and the through holes 5a and 5b are provided at a corner of the plate 4-3.

Figure 3A:
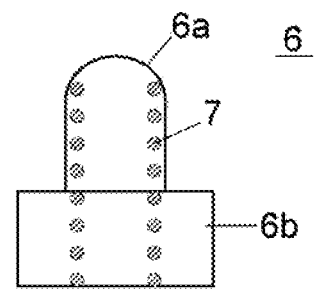
FIGS. 3A and 3B are views for explaining operation of a contact member of the embodiment, where
Figure 3B:
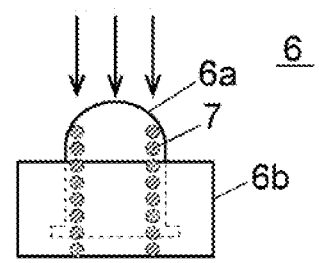

As illustrated in FIGS. 3A and 3B, the contact member 6 is constituted of a projection 6a and a main body 6b that holds a base end of the projection 6a. The projection 6a is provided so as to be displaced in the vertical direction relative to the main body 6b. The projection 6a is supported by an elastic member 7 such as a coil spring that expands and contracts in the vertical direction, and when a downward external force acts on a tip portion of the projection 6a, the projection 6a is elastically displaced vertically downward relative to the main body 6b. Since the projection 6a of the contact member 6 is elastically displaced, when the contact member 6 is moved in a horizontal direction with the tip portion of the projection 6a being in contact with the palm of the subject arranged on the plate 4, the tip portion of the projection 6a moves up and down following irregularities of the palm of the subject.

Figure 4:
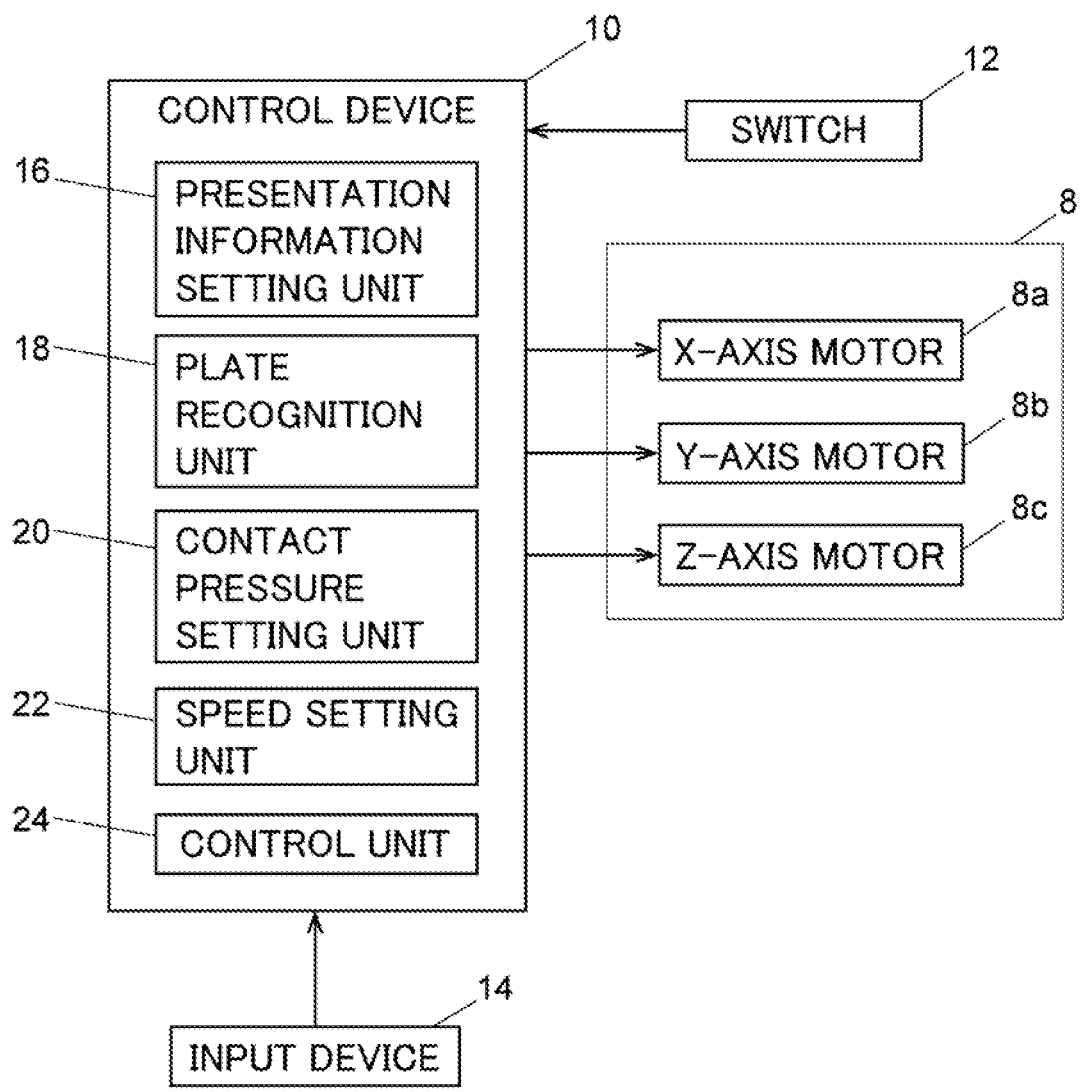
FIG. 4 is a block diagram illustrating a configuration of the same embodiment.

As illustrated in FIG. 4, the tactile stimulus presentation device includes a control device 10 for controlling operation of the drive mechanism 8. The control device 10 is implemented by an electronic circuit on which an arithmetic element, a storage memory, and so on are mounted. The control device 10 includes an information setting part 16, a plate recognition part 18, a contact pressure setting part 20, a speed setting part 22, and a control part 24. The information setting part 16, the plate recognition part 18, the contact pressure setting part 20, the speed setting part 22, and the control part 24 are functions that are obtained when the arithmetic element executes a predetermined program.

The information setting part 16 is configured to set information to be presented to the subject by tactile stimulation based on information input by an experimenter via an input device 14. The control device 10 holds information about a control method of the drive part 8 for causing the contact member 6 to write predetermined characters and symbols, and the experimenter can select a character or symbol desired to be presented to the subject as presentation information from among those characters and symbols. For example, in the case of the Sumanu ( スマヌ ) method, Japanese characters such as " ス " (su), " マ " (ma), and " ヌ " (nu) can be selected and set as presentation information, but if information about other characters and symbols are registered in the control device 10, various characters and symbols can be set as presentation information. Further, the experimenter can input a plurality of characters and symbols and a presentation order thereof, and the information setting part 16 is configured to set the characters and symbols and the presentation order input by the experimenter as the presentation information.

The plate recognition part 18 is configured to recognize, based on a signal from the switch 12, which of the plates 4-1 to 4-3 the plate 4 placed on the housing 2 is.

The contact pressure setting part 20 is configured to set, based on contact pressure information input by the experimenter via the input device 14, a contact pressure given by the contact member 6 to the palm of the subject when the contact member 6 writes a character or symbol on the palm of the subject. The contact pressure can be adjusted by changing a sending position in the Z-axis direction of the drive mechanism 8 when writing a character or symbol on the palm of the subject by the contact member 6. The control device 10 is provided with multiple levels of contact pressures, and the experimenter can select a desired level from these levels.

The speed setting part 22 is configured to set, based on the contact pressure information input by the experimenter via the input device 14, driving speeds in the X-axis direction and the Y-axis direction of the drive mechanism 8 when writing a character or symbol on the palm of the subject by the contact member 6. The control device 10 is provided with multiple levels of driving speeds, and the experimenter can select a desired level from these levels.

The control part 24 is configured to perform operation control of an X-axis motor 8a, a Y-axis motor 8b, and a Z-axis motor 8c of the drive mechanism 8 based on the presentation information set by the information setting part 16, the type of the plate 4 recognized by the plate recognition part 18, the contact pressure set by the contact pressure setting part 20, and the driving speed set by the speed setting part 22. Specifically, the control part 24 recognizes the size of the opening 4a of the plate 4 based on the type of the plate 4 recognized by the plate recognition part 18, and controls operation of the X-axis motor 8a, the Y-axis motor 8b, and the Z-axis motor 8c so that presentation information (character or symbol) set by the information setting part 16 is written on the palm of the subject within the range of the size of the opening 4a. The height position of the contact member 6 when writing presentation information on the palm of the subject is adjusted based on the level of the contact pressure set by the contact pressure setting part 20, and the moving speed of the moving speed 6 when writing presentation information on the palm of the subject is adjusted based on the level of the driving speed set by the speed setting part 22.

Note that the X-axis motor 8a is a motor for moving the contact member 6 in the X-axis direction, the Y-axis motor 8b is a motor for moving the contact member 6 in the Y-axis direction, and the Z-axis motor 8c is a motor for moving the contact member 6 in the Z-axis direction.

Note that the plate recognition part 18 is not an essential component. Even when the plate recognition part 18 is not provided, the control part 24 can recognize the size of the opening of the plate 4 by the experimenter inputting information on the type of the plate 4 placed on the housing 2 to the control device 10.

Moreover, the contact pressure setting part 20 and the speed setting part 22 are not essential components.

Further, in the above embodiment, the size of the opening 4a can be changed according to the size of the palm of the subject by using a plate 4 arbitrarily selected from a plurality of types of plates 4-1 to 4-3. However, the present invention is not limited to this, and it is not necessary that the size of the opening can be changed.

Further, in the above embodiment, the palm is arranged on the upper surface of the plate 4 as a body part of the subject. However, the present invention is not limited to this, and the body part of the subject to be arranged on the upper surface of the plate 4 may be any part as long as tactile stimulation can be given to the subject.

Further, in the above embodiment, the arrangement surface (the upper surface of the plate 4) on which a body part of the subject is arranged is a horizontal surface. However, the present invention is not limited to this, and the arrangement surface may be inclined with respect to the horizontal direction. In that case, the drive mechanism 8 is configured to move the contact member 6 in a direction substantially parallel to the arrangement surface on which a body part of the subject is arranged and in a direction substantially perpendicular to the arrangement surface.

DESCRIPTION OF REFERENCE SIGNS 2 housing
2a opening
4, 4-1, 4-2, 4-3 plate
4a, 4a-1, 4a-2, 4a-3 opening
5a, 5b through hole
6 contact member
6a projection
6b main body
7 elastic member
8 drive mechanism
8a X-axis motor
8b Y-axis motor
8c Z-axis motor
10 control device
12 switch
14 input device
16 information setting part
18 plate recognition part
20 contact pressure setting part
22 speed setting part
24 control part

What is claimed is:

1. A tactile stimulus presentation device comprising:
a stage that has an opening and an arrangement surface on which a body part of a subject is arranged thereon so as to close the opening;
a contact member for giving a tactile stimulus to the subject by being in contact with the body part of the subject arranged on the arrangement surface of the stage through the opening;
a drive mechanism that holds the contact member and moves the contact member in a direction substantially parallel to the arrangement surface and in a direction substantially perpendicular to the arrangement surface;
an information setting part configured to set information, which includes a character or a symbol, to be presented by giving tactile stimulation to the subject; and
a control part configured to control the drive mechanism so that the information including the character or the symbol set by the information setting part is written on the body part of the subject arranged on the arrangement surface.

2. The tactile stimulus presentation device according to claim 1, further comprising a contact pressure setting part configured to set a contact pressure by the contact member to the body part of the subject arranged on the arrangement surface, wherein the control part is configured to control the drive mechanism so as to adjust a contact pressure by the contact member to the body part of the subject arranged on the arrangement surface to the contact pressure set by the contact pressure setting part.

3. The tactile stimulus presentation device according to claim 1, further comprising a speed setting part configured to set a speed at which the drive mechanism moves the contact member in a direction substantially parallel to the arrangement surface, wherein the control part is configured to control the drive mechanism to move the contact member in a direction substantially parallel to the arrangement surface at the speed set by the speed setting part.

4. The tactile stimulus presentation device according to claim 1, wherein the contact member is configured so that a tip thereof is elastically displaced by an external force in a direction substantially perpendicular to the arrangement surface.

5. A tactile stimulus presentation device comprising:
a stage that has an opening and an arrangement surface on which a body part of a subject is arranged thereon so as to close the opening;
a contact member for giving a tactile stimulus to the subject by being in contact with the body part of the subject arranged on the arrangement surface of the stage through the opening;
a drive mechanism that holds the contact member and moves the contact member in a direction substantially parallel to the arrangement surface and in a direction substantially perpendicular to the arrangement surface;
an information setting part configured to set information to be presented by giving tactile stimulation to the subject; and
a control part configured to control the drive mechanism to present the information set by the information setting part by giving tactile stimulation to the body part of the subject arranged on the arrangement surface;
wherein
the stage is formed by a plate supported at a predetermined position by a plate support part, and the plate supported by the plate support part is a plate arbitrarily selected from a plurality of types of plates having different sizes of the opening, the tactile stimulus presentation device further comprises a plate recognition part configured to recognize a type of the plate supported by the plate support part, and the control part is configured to control the drive mechanism so as to present, by giving tactile stimulation to a subject, information of a size corresponding to a size of the opening of the plate recognized by the plate recognition part.

6. The tactile stimulus presentation device according to claim 5, wherein each of the plurality of types of plates has a through hole at a different position thereof from each other or has a different number of through holes, and the plate recognition part is configured to recognize a type of the plate supported by the plate support part by detecting the position of the through hole of the plate or the number of through holes of the plate supported by the plate support part using a switch.

7. The tactile stimulus presentation device according to claim 1, wherein the arrangement surface is configured so that a palm of the subject is arranged as the body part.

8. The tactile stimulus presentation device according to claim 1, wherein the stage is formed by a plate supported at a predetermined position by a plate support part, and the plate supported by the plate support part is a plate arbitrarily selected from a plurality of types of plates having different sizes of the opening, the tactile stimulus presentation device further comprises a plate recognition part configured to recognize a type of the plate supported by the plate support part, and the control part is configured to control the drive mechanism so as to write information on the body part of the subject at a size corresponding to a size of the opening of the plate recognized by the plate recognition part.

9. The tactile stimulus presentation device according to claim 8, wherein each of the plurality of types of plates has a through hole at a different position thereof from each other or has a different number of through holes, and the plate recognition part is configured to recognize a type of the plate supported by the plate support part by detecting the position of the through hole of the plate or the number of through holes of the plate supported by the plate support part using a switch.

10. The tactile stimulus presentation device according to claim 1, further comprising an elastic member configured to support the contact member; the elastic member allowing the contact member to remain in contact the body part regardless of irregularities in the shape of the body part.

11. The tactile stimulus presentation device according to claim 10, wherein the elastic member is a coil spring.

* * * * *